United States Patent
Greenbaum et al.

(10) Patent No.: US 11,529,301 B2
(45) Date of Patent: Dec. 20, 2022

(54) CANNABINOID ENRICHED PERSONAL LUBRICANT

(71) Applicant: RESURGENT BIOSCIENCES, INC., Minneapolis, MN (US)

(72) Inventors: Eric Greenbaum, Denver, CO (US); Justin Bueno, Albany, NY (US); Emily Leuer, Minneapolis, MN (US); Kyle Kingsley, Minneapolis, MN (US)

(73) Assignee: Resurgent Biosciences, Inc., Minneapolis, MN (US)

( * ) Notice: Subject to any disclaimer, the term of this patent is extended or adjusted under 35 U.S.C. 154(b) by 0 days.

(21) Appl. No.: 16/986,550

(22) Filed: Aug. 6, 2020

(65) Prior Publication Data

US 2021/0038493 A1 Feb. 11, 2021

Related U.S. Application Data

(60) Provisional application No. 62/883,634, filed on Aug. 6, 2019.

(51) Int. Cl.
| | | |
|---|---|---|
| *A61K 8/34* | (2006.01) | |
| *A61K 8/60* | (2006.01) | |
| *A61K 8/73* | (2006.01) | |
| *A61K 9/00* | (2006.01) | |

(52) U.S. Cl.
CPC .............. *A61K 8/735* (2013.01); *A61K 8/345* (2013.01); *A61K 8/347* (2013.01); *A61K 8/60* (2013.01); *A61K 8/731* (2013.01); *A61K 8/738* (2013.01); *A61K 9/0034* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,885,591 A * | 3/1999 | Ahmad | A61K 9/0034 424/400 |
| 2016/0017254 A1* | 1/2016 | Cojocariu | A61F 6/04 508/309 |
| 2016/0220593 A1* | 8/2016 | Anastassov | A23G 1/40 |
| 2017/0266127 A1* | 9/2017 | Denniston, V | A61K 31/51 |

* cited by examiner

*Primary Examiner* — Kyung S Chang
(74) *Attorney, Agent, or Firm* — Dicke, Billig & Czaja, PLLC

(57) ABSTRACT

A composition and methods for lubricating mucous membranes including reproductive tissue with a topical lubricant and at least one cannabinoid. Cannabis and cannabinoids are solubilized and combined with water-based personal lubricants.

2 Claims, No Drawings

CANNABINOID ENRICHED PERSONAL LUBRICANT

This application claims benefit of U.S. Provisional Application No. 62/883,634, filed on Aug. 6, 2020 and which application is incorporated herein by reference. A claim of priority is made.

FIELD OF THE INVENTION

The invention relates generally to cannabis formulations and products adapted to increase the lubricity of mucous membranes.

BACKGROUND OF THE INVENTION

Lubrication is the process or technique that reduces wear of one or both surfaces that move relative to each other in close proximity Lubricants prevent or lessen wear and irritation between the surfaces.

Personal lubricants for enhancing personal and/or sexual congress are well known and are useful for providing lubricity to various parts of the body, such as mucous membranes (e.g. oral, rectal, vaginal). These compositions may be in the form of jellies, liquids, vaginal suppositories, oils or emulsions. When applied onto condoms, these lubricants also facilitate unrolling of the condom as well as preventing the surfaces of the rolled condom from sticking together as the products age in storage.

Water-based personal lubricants are water-soluble and are the most widely used personal lubricants. These lubricants are easy to clean up, non-staining to fabrics and are formulated to be nonirritating.

Cannabis and cannabinoids have demonstrated the ability to enhance the sexual experience, mitigate certain sexual dysfunctions, relax the body and mind, and provide other meaningful health benefits. Furthermore, cannabis and cannabinoids may be readily absorbed into the body via mucous membranes.

While cannabis and cannabinoids, from medical, pharmacological, and toxicological standpoints are remarkably safe, the overconsumption of cannabinoids contained in cannabis, and in particular tetrahydrocannabinol ("THC,") can be associated with a variety of unpleasant side effects. These overconsumption effects include paranoia, intense anxiety, hyperemesis, and several others. The experience of THC overconsumption can be so unpleasant, that often, a single negative experience is sufficient to turn somebody off of cannabis use for life. Therefore, it is important to provide cannabis products packaged and dosed in such a manner as to facilitate responsible, controlled, consumption.

SUMMARY

As specified in the Background Section above, there is a need in the art to develop water soluble personal lubricant formulations containing cannabinoids, in some cases, in fixed individual dosage format, for the purposes of increasing sexual pleasure and addressing sexual dysfunction. Therefore, the inventors herein present:

A topical lubricant composition made up of an aqueous lubricant base adapted for topically lubricating reproductive tissue, and further containing at least one cannabinoid selected from the group consisting of THC, CBD, THCA, CBDA, CBC, CBG, and THCV A composition for lubricating mucous membranes made of a water-soluble mixture adapted to increase the lubricity of mucous membranes and containing at least one cannabinoid selected from the group consisting of THC, CBD, THCA, CBDA, CBC, CBG, and THCV A composition for lubricating mucous membranes made up of glycerin, propylene glycol, at least one sugar alcohol, at least one preservative, a hydrocolloid, water, and a water solubilized cannabinoid mixture.

A composition for lubricating mucous membranes made of: from about 5 to about 50% by weight of glycerin, from about 2 to about 40% by weight of propylene glycol, from about 5 to about 25% by weight of a sugar alcohol, from about 0.25 to about 1% by weight of water-soluble cellulose gum, and further comprising at least one cannabinoid selected from the group consisting of THC, CBD, THCA, CBDA, CBC, CBG, CBN, and THCV.

An aqueous lubricant composition made of a salt selected from the group consisting of sodium chloride, potassium chloride, and mixtures thereof; an organic acid selected from the group consisting of acetic acid, citric acid, their salts and mixtures thereof; hyaluronic acid having a molecular weight of between 1.3 MDa and 1.8 MDa; a hydrocolloid; at least one cannabinoid that has been treated to make it water soluble and water, wherein the water is present in an amount of at least 90 wt. % of the composition.

A blow-fill-seal method of producing individual dose portions of a cannabinoid containing personal lubricant made up of the steps of forming a container; filling the formed container with a personal lubricant which further comprises at least one cannabinoid; and sealing the container.

An individual dose portion of a personal lubricant made up of a chamber of suitable size to hold a pre-determined volume of the personal lubricant suitable to provide sufficient personal lubrication and deliver a desired dose of cannabinoid(s), a quantity of personal lubricant formulation further comprising at least one cannabinoid stored within the chamber; a neck in fluid communication with the chamber, a sealing member attached to the neck to seal the neck against the environment and prevent a fluid from exiting the chamber; and wherein the sealing member is manually removable to expose the neck and allow the personal lubricant formulation in the chamber to be dispensed.

A method of making a lubricant composition made up of the steps of: first mixing the water soluble ingredients; then adding preservatives to the water soluble mixture in the same container; then adding to the container a water-soluble polymer derived from cellulose and mixing the composition until it becomes a slurry; then adding at least one cannabinoid that has been suitably processed to be water soluble; and then adding water and mixing.

A method for treating and/or preventing microbiological infections of the reproductive organs comprising the steps of administering a pharmacologically effective amount of a personal lubricant formulation further comprising at least one cannabinoid.

DETAILED DESCRIPTION

These and other systems, methods, objects, features, and advantages of the present disclosure will be apparent to those skilled in the art from the following detailed description of the embodiments and drawings. All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from context The cannabinoids are a class of molecules found in cannabis plant material, although they can also be made synthetically or in bioreactors. The various cannabinoids include tetrahydrocannabinol (THC), cannabidiol (CBD), ("the major cannabinoids"), tetrahydrocannabinolic acid (THCA), Cannabidiolic acid (CBDA), cannabinol (CBN), cannabigerol (CB G), cannabichromene (CBC), tetrahydrocannabivarin (THCV), and cannabidivarin (CBDV) as well as others ("the minor cannabinoids"). Various cannabinoids, used alone or in combination have shown a variety of significant biological effects including but not limited to pain relief, anti cancer, anti inflammatory, anti emetic, anti-convulsant, anti-microbial, and many others, including recreational effects. Of particular significance for this disclosure is the tendency of some cannabinoids to affect sexual performance and/or pleasure.

Personal lubricant base formulations suitable for use with the present invention are generally known in the art and can be quite varied. Some exemplary ingredient lists include but are not limited to the following. While these ingredient lists are listed as separate examples, it should be understood that any of the listed ingredients and others known to those having skill in the art may be used to make the lubricant base formulation:

Example 1: Purified Water, Glycerin, Propylene Glycol, Polyquaternium 15, Methylparaben, Propylparaben.

Example 2: Purified Water, Glycerin, Hydroxyethylcellulose, Chlorhexidine Gluconate, Methylparaben, Glucono Delta Lactone, Sodium Hydroxide.

Example 3: Purified Water, Propylene Glycol, Hydroxyethylcellulose, Caprylyl Glycol, Caprylhydroxamic Acid, Propanediol, Polyquaternium 15, Lactic Acid.

Example 4: Dimethicone, Cyclomethicone, Dimethicone/Vinyl Dimethicone Crosspolymer, Caprylic/Capric Triglyceride.

Example 5: Cyclomethicone, Dimethicone.

Example 6: Purified Water, Xylitol, Aloe Barbadensis Leaf Juice, Pectin, Chamomilla Recutita (Matricaria) Flower Extract, Potassium ascorbyl tocopheryl phosphate (Vitamins C & E), Lactic Acid, Hydroxyethylcellulose, Phenoxyethanol.

Example 7: Purified Water, Glycerin, Propylene Glycol, Hydroxyethylcellulose, Natural & artificial Strawberry Flavor, Sodium Gluconate, Sodium Saccharin, Methylparaben, Sodium Benzoate, Citric Acid.

Example 8: Purified Water, Propylene Glycol, Hydroxyethylcellulose, Fructose, Galactose, Potassium Phosphate, Sodium Phosphate, Methylparaben, Propylparaben, Sodium Hydroxide.

Example 9: Water (Aqua), Propanediol, Gluconolactone, Hydroxyethylcellulose, Sodium Benzoate, Citric Acid.

Example 10: Propylene Glycol, Water (Aqua), Phenoxyethanol, Dimethicone, Cellulose Gum, Cyclopentasiloxane, Sodium Polyacrylate Trideceth-6, PEG/PPG-18/18 Dimethicone.

Example 11: Aloe Barbadensis Leaf Juice, Xanthan Gum, Lactic Acid, Natural Flavor, Potassium Sorbate, Sodium Benzoate.

Example 12: Aloe Barbadensis Leaf Juice, Xanthan Gum, Carrageenan, Organic-compliant flavor (EU: Aroma), Lactic Acid, Potassium Sorbate, Sodium Benzoate, Dimethyl Isosorbide.

Example 13: Aloe Barbadensis Leaf Juice, Xanthan Gum, Agar, Potassium Sorbate, Sodium Benzoate, Sodium Lactate, Lactic Acid, Natural Food Grade Flavors (Lemon and Vanilla).

Example 14: Water/Aqua/Eau, Glycerin, Propylene Glycol, Cellulose Gum, EDTA, Carbomer, PEG-90M, Tetrahydroxypropyl Ethylenediamine, Methylparaben, Sodium Benzoate, Potassium Sorbate.

Example 15: Cyclopentasiloxane, Dimethicone And Dimethiconol.

Example 16: Water, glycerin, propylene glycol, sorbitan stearate, isopropyl myristate, cetearyl alcohol, polysorbate 60, hydrolyzed silk, sodium hyaluronate, cyclopentasiloxane, carbomer, dimethicone, EDTA, hydroxyethylcellulose, PEG-45M, tetrahydroxypropyl ethylenediamine, methylparaben, sodium benzoate.

Example 17: Water (Aqua), Glycerin, Potassium Sorbate, Hydroxyethylcellulose, Flavor (Aroma), Sucralose, Sodium Chloride, Citric Acid.

Example 18: Dimethicone, Cyclopentasiloxane, Cyclotetrasiloxane, Dimethiconol.

Example 19: Glycerin, Water (Aqua), Cellulose Gum, Methylparaben, Propylparaben.

Example 20: Water, Propylene Glycol, Sorbitol, Polysorbate 60, Hydroxyethylcellulose, Benzoic acid, Tocopheryl acetate.

Example 21: Glycerin, Propylene Glycol, Maltodextrin, Honey, Methylparaben, Sucralose.

Example 22: Water, Glycerin, Hydroxyethylcellulose, Chlorhexidine Gluconate, Gluconolactone, Methylparaben, Sodium Hydroxide.

Exampled 23: Water, Glycerin, Sorbitol, Propylene Glycol, Hydroxyethylcellulose, Benzoic Acid, Methylparaben, Sodium Hydroxide.

Example 24: Glycerin, Propylene Glycol, Maltodextrin, Honey, Methylparaben, Sucralose.

Example 25: Water, Propylene Glycol, Polysorbate 20, Hydroxyethylcellulose, Benzoic Acid, Menthyl Lactate, Methyl Salicylate, Fragrance, Sodium Hydroxide.

Example 26 Glycerin, Propylene Glycol, Maltodextrin, Honey, Methylparaben, Sucralose.

Example 27: Dimethicone, Dimethiconol, Gelatin, Glycerin.

Example 28: Water (USP Purified), Glycerin, Polycarbophil, Carbomer Homopolymer (Type B), Ethylparaben Sodium, Methylparaben Sodium, Propylparaben Sodium, Sodium Hydroxide.

Example 29: Deionised water, hypromellose, sodium chloride, glycerol, sodium phosphate, disodium phosphate, methylparaben, potassium chloride, magnesium chloride, calcium chloride.

Example 30: Organic Aloe Barbadensis Leaf Juice (reconstituted Aloe vera), Xanthan Gum, Agar, Potassium Sorbate and Sodium Benzoate, Lactic Acid, Natural Flavors.

Example 31: Organic Aloe Barbadensis Leaf Juice (reconstituted Aloe vera), Xanthan Gum, Agar, Potassium Sorbate and Sodium Benzoate, Lactic Acid, Natural Flavors.

Example 32: Aqua (water), Aloe barbadensis (Aloe vera)*, Cyamopsis tetragonolobus (Guar Gum), Ceratonia siliqua (Locust Bean Gum)*, Linum usitatissimum (Flax extract), Phenoxyethanol, Potassium sorbate, Xanthan Gum, Citric acid.

Example 33: at least one polyhydric alcohol which is water-soluble, a water-soluble polymer derived from cellulose, tocopherol or a tocopherol derivative, a nonionic emulsifier and water.

In some embodiments, warming/cooling/tingle/ensitivity reducing agents are added to enhance the overall experience of the personal lubricant. These agents are known in the art.

In some embodiments absorption enhancing agents are added to the lubricant formulation to enhance absorption of the cannabinoid(s) across the skin and or mucous membranes of the users.

The water absorbing polymer hyaluronic acid ("HA") is used in some embodiments. The pharmaceutically acceptable salts of hyaluronic acid include both the salts with inorganic bases (e.g. sodium salt, potassium salt, ammonium salt, etc.) and the salts with organic bases (e.g. diethanolamine salt, cyclohexylamine salt, amino acid salt, etc.). Preferred salts are dermatologically acceptable ones. Typically, the HA of some embodiments of the present aqueous lubricant composition is obtained from animal sources or from bioprocesses, including via bacterial or enzyme synthesis. Suitably, the HA of the lubricant of the present invention is obtained from fermentation or enzymatic synthesis.

An embodiment of the present aqueous lubricant composition comprises HA produced from the microorganism *Bacillus subtilis*, or by fermentation of *Streptococcus* species. Suitably all of the HA of the present aqueous lubricant composition is produced by fermentation of a *Streptococcus* sp.

The purity of HA is partially or wholly dependent on its source and its method of production. Typically, the purity of the HA used is at least 70%, preferably at least 85% and more preferably at least 90%. In particular, the HA used in the lubricant of the present invention suitably includes a heavy metal impurity level of less than 10 ppm, advantageously less than 5 ppm.

Further, the HA may be modified or unmodified. Useful HA may be modified by crosslinking to obtain at least one low level functional group or at least one peptide. The HA for the embodiments of the present aqueous lubricant is preferably unmodified. The preferred hyaluronic acid has a molecular weight of 40 kDa to 3 MDa, preferably 800 kDa to 2.0 MDa, more preferably 1.3 MDa to 1.8 MKDa. The moisturizing agent is present in an amount of from about 0.05 wt. % to about 5.00 wt. %, preferably from about 0.1 wt. % to about 2.0 wt. %, more preferably from about 0.4 wt. % to about 1.0 wt. % of the aqueous lubricant composition.

A rheology modifier is used in some embodiments of the present invention and may be selected from dimeric and trimeric fatty acids, amides, synthetic polymers and mixtures thereof. Preferably, the rheology modifier is a water-soluble polymer such as modified cellulose, selected from hydroxyethyl cellulose, carboxymethyl cellulose, hydroxypropyl cellulose, methylcellulose and mixtures thereof. More preferably, the rheology modifier is hydroxyethyl cellulose. The rheology modifier is present in an amount from about 0.05 wt. % to about 5.00 wt. %, preferably from about 0.1 wt. % to about 3.0 wt. %, and more preferably from about 0.3 wt. % to about 2.0 wt. % of the aqueous lubricant composition.

In an embodiment silicone oils and silicone polymers (such as, for example polysiloxanes) are specifically avoided in order to facilitate compatibility with silicone-based pleasure devices that may be degraded by silicone containing formulations. In other embodiments silicone oils/compounds are included in the formulations for their unique lubricity characteristics.

In some embodiments the cannabinoid(s) require solubilization in order to be incorporated into the aqueous personal lubricant formulation. In specific embodiments the cannabinoid(s) are made more water soluble through complexation with cyclodextrins, including both natural and modified cyclodextrins, such as, for example, a sulfobutylether □-cyclodextrins such as CAPTISOL. In specific embodiments the cannabinoids are made more water soluble through emulsification such as, for example, nano or micro emulsification. In specific embodiments the other ingredients of the personal lubricant are selected, and the formulation created, to be a suitable diluent for the desired amount of cannabinoids without further complexation or modification. In specific embodiments the cannabinoids are released from complexation under in vivo conditions allowing for pharmaceutical and/or recreational efficacy, and improving the stability of the water soluble cannabinoid formulation.

In specific embodiments the cannabinoid(s) are made more water soluble through complexation with a sugar alcohol, such as, for example isomalt. An exemplary method comprises: combining a cannabis extract, such as, for example, cannabis oil distillate with ethanol and sonicating to facilitate homogenization; heating isomalt until melted in a beaker or other suitable mixing vessel until a clear, uniform, liquid results; adding quillaja extract or other suitable emulsifying agent or surfactant to liquid isomalt; adding the cannabis/ethanol solution to the molten isomalt; stirring resulting mixture with heat to achieve a homogenous mixture; pouring cannabinoid/isomalt mixture onto suitable cooling surface, such as a silicone sheet or mold; allowing to cool, and breaking up cooled mixture into roughly 1 inch pieces; milling pieces to powder. At this point the isomalt powder may be added to the lubricant formulations.

In an embodiment, the cannabinoid(s) are solubilized using a sulfobutylether cyclodextrin, such as, for example, CAPTISOL. This process may be accomplished in a variety of ways such as, for example, by first creating a cannabinoid(s) tincture by dissolving a cannabis extract or isolated cannabinoids into an alcohol such as ethanol. A cyclodextrin(s) solution is created separately by dissolving the cyclodextrin(s) into water or an appropriate buffer. Next, the cyclodextrin(s) solution is mixed with the cannabinoid(s) tincture. Next, the ethanol is removed via evaporation or other suitable method leaving behind an aqueous solution containing cannabinoid(s) that can then be mixed into the lubricant formulation.

In various embodiments, cannabinoid(s) are present in various ratios and amounts. Generally speaking, the ratio of THC to CBD will be controlled and may exist in the range of 1:100 to 100:1. In some embodiments from about 1:50 and 50:1. In some embodiments from about 1:25 and 25:1. In some embodiments from about 1:10 to 10:1. In some embodiments from about 1:5 to 5:1. In some embodiments about 1:1. Various other cannabinoids are added to some embodiments to fine-tune the effects of the formulation. Regarding quantities of cannabinoid(s) in the formulations, about 0.1 mg-30 mg cannabinoids per gram of formulation. Ideally the formulations should be created to deliver between 0.5 and 30 mg total cannabinoid(s) per use. The specific concentrations needed to deliver this dose will depend on the characteristics of the formulations and the anticipated quantity of the formulation needed for optimal personal lubrication.

In order to provide accurate, repeatable, cannabinoid(s) dosing, some embodiments of the present invention further comprise individual dose packaging. This packaging presentation is also useful to facilitate cleanliness and hygiene of the packaged formulations. Various packaging means to affect individual use portioning are known in the art. In specific embodiments individual dose portions are packaged via a blow-fill-seal ("BFS") process. In some embodiments the formulations are packaged in "stick packs."

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

With respect to the above, it is to be understood that the invention is not limited in its application to the details of construction and to the arrangement of the components listed or the steps set forth in the description or illustrated in the drawings. The various apparatus and methods of the disclosed invention are capable of other embodiments, and of being practiced and carried out in various ways that would be readily known to those skilled in the art, given the present disclosure. Further, the terms and phrases used herein are for descriptive purposes and should not be construed as in any way limiting.

As such, those skilled in the art will appreciate that the conception upon which this disclosure is based may be utilized as a basis for designing other inventions with similar properties. It is important therefore that the embodiments, objects, and claims herein, be regarded as including such equivalent construction and methodology insofar as they do not depart from the spirit and scope of the present invention.

What is claimed is:

1. A composition for lubricating mucous membranes consisting of:
   about 30% glycerin,
   about 5% propylene glycol,
   about 10% isomalt,
   a surfactant or emulsifying agent,
   about 0.4% preservative,
   about 0.4% hydroxyethylcellulose,
   about, 0.01% sodium hydroxide,
   about 50% water, and
   at least one cannabinoid selected from the group consisting of tetrahydrocannabinol (THC), cannabidiol (CBD), tetrahydrocannabinolic acid (THCA), cannabidiolic acid (CBDA), cannabinol (CBN), cannabigerol (CBG), cannabichromene (CBC), and tetrahydrocannabivarin (THCV); wherein the at least one cannabinoid is complexed with the isomalt in the presence of the surfactant or emulsifying agent.

2. The composition of claim 1, wherein the surfactant or emulsifying agent is quillaja extract.

* * * * *